(12) United States Patent
Gray et al.

(10) Patent No.: US 7,785,813 B2
(45) Date of Patent: Aug. 31, 2010

(54) PREFOLDIN 4 IN THE TREATMENT AND DIAGNOSIS OF CANCER

(75) Inventors: Joe Gray, San Francisco, CA (US); Graeme Hodgson, San Francisco, CA (US); Douglas Hanahan, San Francisco, CA (US); Jeffrey Hager, San Diego, CA (US); Oriol Casanovas, Barcelona (ES)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 11/471,464

(22) Filed: Jun. 19, 2006

(65) Prior Publication Data

US 2007/0015724 A1 Jan. 18, 2007

Related U.S. Application Data

(60) Provisional application No. 60/692,847, filed on Jun. 20, 2005.

(51) Int. Cl.
*G01N 33/53* (2006.01)
*A61K 48/00* (2006.01)
*C12Q 1/68* (2006.01)

(52) U.S. Cl. ..................................... 435/7.23
(58) Field of Classification Search .................. 435/7.23
See application file for complete search history.

(56) References Cited

U.S. PATENT DOCUMENTS

| 6,812,339 | B1 * | 11/2004 | Venter et al. | 536/24.31 |
| 2004/0053277 | A1 * | 3/2004 | Zhang et al. | 435/6 |
| 2006/0275794 | A1 * | 12/2006 | Carrino et al. | 435/6 |
| 2006/0281122 | A1 * | 12/2006 | Bryant et al. | 435/6 |

OTHER PUBLICATIONS

Search output from Human Protein Reference Database for "prefoldin 4".*
Search output from OMIM database for "prefoldin 4".*
Sequence search alignment showing the sequence match with SEQ ID No. 10,180 of Venter (US 6,812,339).*
Sequence search alignment with SEQ ID No. 57, 671 of Carrino (US 20060275794).*
Collins et al. (Genome Res. 11:1034 (2001)).*
Albertson, "Quantitative mapping of amplicon structure by array CGH identifies CYP24 as a candidate oncogene," 2000, Nature Genetics, 25:144-146.
Bhattacharjee et al., Classification of human lung carcinomas by mRNA expression profiling reveals distinct adenocarcinoma subclasses, 2001, Proc. Natl. Acad. Sci USA, 98: 13790-13795.
Collins et al., "Comprehensive Genome Sequence Analysis of Breast Cancer Amplicon," 2001, Genome Res., 11:1034-1042.
Collins, "Positional cloning of *ZNF217* and *NABC1*: Genes amplified at 20q13.2 and overexpressed in breast carcinoma," 1998, Proc. Natl. Acad. Sci USA, 95:8703-8708.
Diebold, "20q13 and cyclin D1 in ovarian carcinomas. Analysis by fluorescence in situ hybridization," 2000, J. Pathol. 190:564-571.
Guan et al., "Recurrent chromosome alterations in hepatocellular carcinoma detected by comparative genomic hybridization," 2000, Genes Chromosomes Cancer, 29: 110-116.
Hager et al., "Oncogene Expression and Genetic Background Influence the Frequency of DNA Copy Number Abnormalities in Mouse Pancreatic Islet Cell Carcinomas," 2004, Cancer Research, 64: 2406-2410.
Harris et al., Comprehensive molecular cytogenetic characterization of cervical cancer cell lines. 2003, Genes Chromosomes Cancer, 36:233-41.
Hidaka, "Differences in 20q13.2 Copy Number between Colorectal Cancers with and without Liver Metastasis," 2000, Clin. Cancer Res., 6:2712-2717.
Ramaswamy, et al., "Multiclass cancer diagnosis using tumor gene expression signatures," 2001, Proc. Natl. Acad. Sci USA, 98, 15149-15154.
Savelieva et al., "20q gain associates with immortalization: 20q13.2 amplification correlates with genome instability in human papillomavirus 16 E7 transformed human uroepithelial cells," 1997, Oncogen, 14:551-560.
Stumpf et al., "Chromosomal alterations in human pancreatic endocrine tumors," 2000, Genes Chromosomes Cancer, 29:83-87.
Tanner et al., "Frequent Amplification of Chromosomal Region 20q12-q13 in Ovarian Cancer," 2000, Clin. Cancer Res. 6:1833-1839.
Weiss et al., "Determination of amplicon boundaries at 20q13.2 in tissue samples of human gastric adenocarcinomas by high-resolution microarray comparative genomic hybridization," 2003, J. Pathol., 200: 320-326.
Zhang et al., "Genetic alterations in cervical carcinomas: frequent low-level amplifications of oncogenes are associated with human papillomavirus infection," 2002, Int. J. Cancer, 101:427-433.
Zhao et al., "Genomic imbalances in the progression of endocrine pancreatic tumors," 2001, Genes and Chromosomes Cancer, 32:364-372.

* cited by examiner

*Primary Examiner*—Lynn Bristol
(74) *Attorney, Agent, or Firm*—Townsend and Townsend and Crew LLP.

(57) ABSTRACT

This invention provides methods employing prefoldin-4 (PFDN-4) nucleic acid and polypeptide sequences to detect cancer or a propensity to develop cancer, to monitor the efficacy of a cancer treatment, and/or for prognostic applications. Further, the invention provides methods of identifying inhibitors of PfDN-4 and methods of treating cancer by inhibiting the expression and/or activity of PFDN-4.

2 Claims, 4 Drawing Sheets

Figure 2: 'In vitro' characterization of βTC cell clones

FIGURE 4

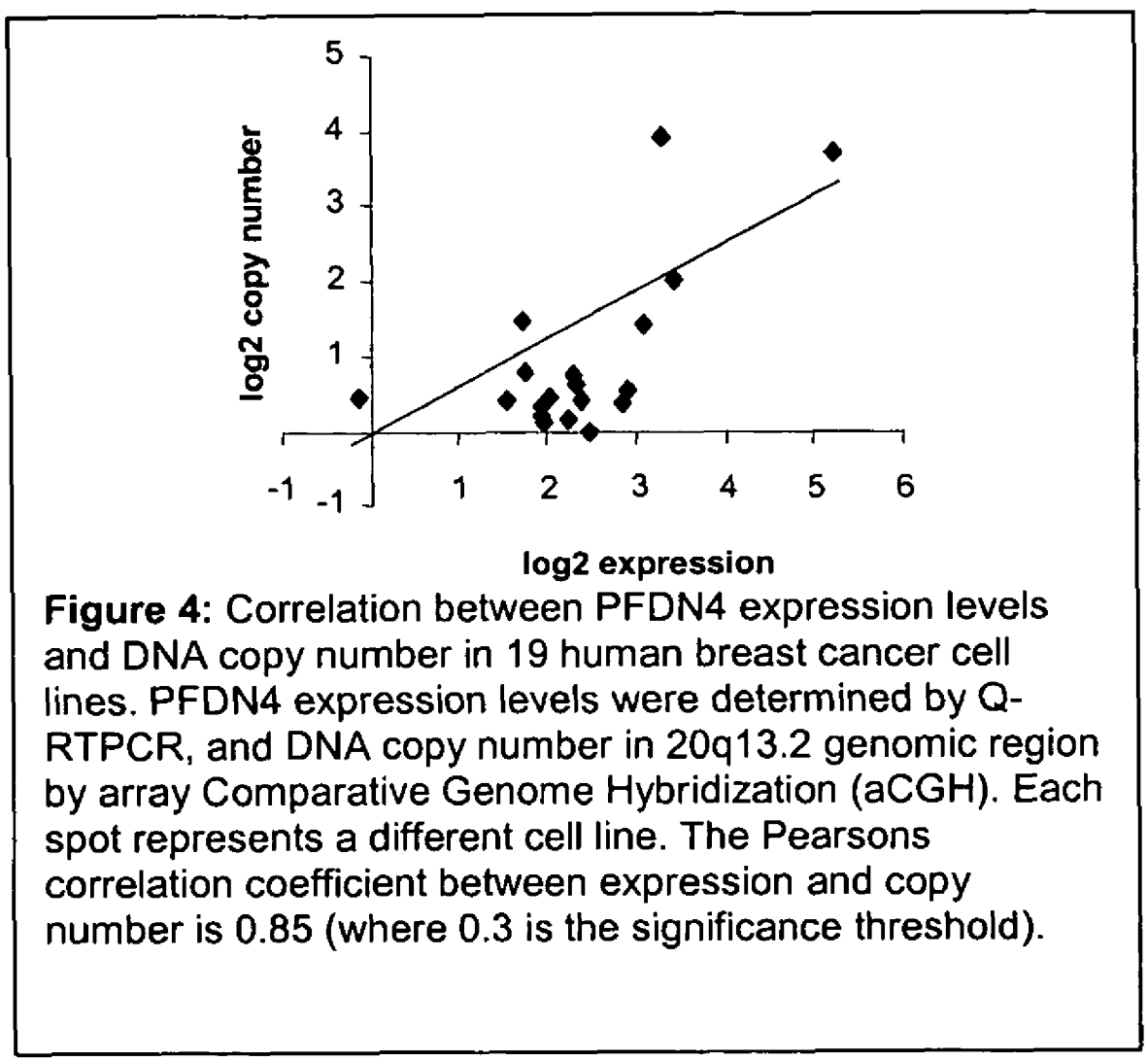

Figure 4: Correlation between PFDN4 expression levels and DNA copy number in 19 human breast cancer cell lines. PFDN4 expression levels were determined by Q-RTPCR, and DNA copy number in 20q13.2 genomic region by array Comparative Genome Hybridization (aCGH). Each spot represents a different cell line. The Pearsons correlation coefficient between expression and copy number is 0.85 (where 0.3 is the significance threshold).

SEQUENCE LISTING

<160> NUMBER OF SEQ ID NOS: 4

<210> SEQ ID NO 1
<211> LENGTH: 500
<212> TYPE: DNA
<213> ORGANISM: Homo sapiens
<220> FEATURE:
<223> OTHER INFORMATION: prefoldin 4 (prefoldin subunit 4, PFDN-4, PFD4,
      protein C-1) cDNA
<220> FEATURE:
<221> NAME/KEY: CDS
<222> LOCATION: (19)..(423)
<223> OTHER INFORMATION: PFDN-4

<400> SEQUENCE: 1

```
ggggagtcca gtcccaag atg gcg gcc acc atg aag aag gcg gct gca gaa      51
                    Met Ala Ala Thr Met Lys Lys Ala Ala Ala Glu
                     1               5                  10 gat gtc aat gtt act ttc gaa gat caa caa aag ata aac aaa ttt gca      99
Asp Val Asn Val Thr Phe Glu Asp Gln Gln Lys Ile Asn Lys Phe Ala
             15                  20                  25 cgg aat aca agt aga atc aca gag ctg aag gaa gaa ata gaa gta aaa     147
Arg Asn Thr Ser Arg Ile Thr Glu Leu Lys Glu Glu Ile Glu Val Lys
         30                  35                  40 aag aaa caa ctc caa aac cta gaa gat gct tgt gat gac atc atg ctt     195
Lys Lys Gln Leu Gln Asn Leu Glu Asp Ala Cys Asp Asp Ile Met Leu
     45                  50                  55 gca gat gat gat tgc tta atg ata cct tat caa att ggt gat gtc ttc     243
Ala Asp Asp Asp Cys Leu Met Ile Pro Tyr Gln Ile Gly Asp Val Phe
 60                  65                  70                  75
```

-continued

```
att agc cat tct caa gaa gaa acg caa gaa atg tta gaa gaa gca aag      291
Ile Ser His Ser Gln Glu Glu Thr Gln Glu Met Leu Glu Glu Ala Lys
            80                  85                  90 aaa aat ttg caa gaa gaa att gac gcc tta gaa tcc aga gtg gaa tca      339
Lys Asn Leu Gln Glu Glu Ile Asp Ala Leu Glu Ser Arg Val Glu Ser
                95                 100                 105 att cag cga gtg tta gca gat ttg aaa gtt cag tta tat gca aaa ttc      387
Ile Gln Arg Val Leu Ala Asp Leu Lys Val Gln Leu Tyr Ala Lys Phe
            110                 115                 120 ggg agc aac ata aac ctt gaa gct gat gaa agt taa acattttata           433
Gly Ser Asn Ile Asn Leu Glu Ala Asp Glu Ser
            125                 130                 135 atactttttt tatttgttta ataaacttga atattgtaaa aaaaaaaaaa aaaaaaaaa     493 aaaaaaa                                                              500
```

<210> SEQ ID NO 2
<211> LENGTH: 134
<212> TYPE: PRT
<213> ORGANISM: Homo sapiens
<220> FEATURE:
<223> OTHER INFORMATION: prefoldin 4 (prefoldin subunit 4, PFDN-4, PFD4, protein C-1)

<400> SEQUENCE: 2

```
Met Ala Ala Thr Met Lys Lys Ala Ala Ala Glu Asp Val Asn Val Thr
 1               5                  10                  15

Phe Glu Asp Gln Gln Lys Ile Asn Lys Phe Ala Arg Asn Thr Ser Arg
                20                  25                  30

Ile Thr Glu Leu Lys Glu Glu Ile Glu Val Lys Lys Gln Leu Gln
            35                  40                  45

Asn Leu Glu Asp Ala Cys Asp Asp Ile Met Leu Ala Asp Asp Cys
    50                  55                  60

Leu Met Ile Pro Tyr Gln Ile Gly Asp Val Phe Ile Ser His Ser Gln
 65                  70                  75                  80

Glu Glu Thr Gln Glu Met Leu Glu Glu Ala Lys Lys Asn Leu Gln Glu
                85                  90                  95

Glu Ile Asp Ala Leu Glu Ser Arg Val Glu Ser Ile Gln Arg Val Leu
            100                 105                 110

Ala Asp Leu Lys Val Gln Leu Tyr Ala Lys Phe Gly Ser Asn Ile Asn
        115                 120                 125

Leu Glu Ala Asp Glu Ser
        130
```

<210> SEQ ID NO 3
<211> LENGTH: 200
<212> TYPE: PRT
<213> ORGANISM: Artificial Sequence
<220> FEATURE:
<223> OTHER INFORMATION: Description of Artificial Sequence:poly-Gly flexible linker
<220> FEATURE:
<221> NAME/KEY: MOD_RES
<222> LOCATION: (6)...(200)
<223> OTHER INFORMATION: Gly at positions 6-200 may be present or absent

<400> SEQUENCE: 3

```
Gly Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly
                20                  25                  30
```

```
Gly Gly Gly Gly Gly Gly Gly Gly Gly Gly Gly Gly Gly Gly
        35                  40                  45
Gly Gly Gly Gly Gly Gly Gly Gly Gly Gly Gly Gly Gly Gly
    50                  55                  60
Gly Gly Gly Gly Gly Gly Gly Gly Gly Gly Gly Gly Gly Gly
 65                  70                  75                  80
Gly Gly Gly Gly Gly Gly Gly Gly Gly Gly Gly Gly Gly Gly
                85                  90                  95
Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly
            180                 185                 190
Gly Gly Gly Gly Gly Gly Gly Gly
        195                 200

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:mRNA coding
      region target sequence double stranded siRNA
      search algorithm 23-nt sequence motif
<220> FEATURE:
<221> NAME/KEY: MOD_RES
<222> LOCATION: (3)...(21)
<223> OTHER INFORMATION: n = g, a, c or t

<400> SEQUENCE: 4
aannnnnnnn nnnnnnnnnn ntt                                          23
```

PREFOLDIN 4 IN THE TREATMENT AND DIAGNOSIS OF CANCER

CROSS-REFERENCE TO RELATED APPLICATIONS

This applications claims benefit of U.S. Provisional Application No. 60/692,847, filed Jun. 20, 2005, which application is herein incorporated by reference.

STATEMENT AS TO RIGHTS TO INVENTIONS MADE UNDER FEDERALLY SPONSORED RESEARCH OR DEVELOPMENT

This invention was made with Government support under grant No. CA45234 awarded by the National Institutes of Health. The Government has certain rights in this invention.

BACKGROUND OF THE INVENTION

Prefoldin 4 (PFDN-4) is a 134 amino acid protein having a helix-loop-helix domain. The protein is a subunit of the heterohexameric chaperone protein prefoldin, a cytoplasmic protein that assists in the correct folding of other proteins, such as actin and tubulin, which are major components of the cellular cytoskeleton. Human PFDN-4 has been localized to chromosome region 20q13. This region is frequently amplified in a variety of human cancers, including breast, ovarian, and cervical cancer. The sequence of the breast cancer amplicon has been analyzed (see, e.g., Collins et al., *Genome Res.* 11:1034-1042, 2001). Although PFDN-4 was identified as one of the genes present in the amplified region and was one of the genes shown to be overexpressed in cell lines in which the amplicon was present, there was no evidence that PFDN-4 played a role in tumorigenicity.

BRIEF SUMMARY OF THE INVENTION

The current invention is based on the discovery that PFDN-4 is amplified during tumor progression and that overexpression of the protein increases tumor growth. PFDN-4 nucleic acid and protein sequences are amplified and overexpressed in cancers, e.g. pancreatic neuroendocrine tumors, breast cancer, ovarian cancer, cervical cancer, gastric adenocarcinomas, uroepithelial tumors, pancreatic islet tumors and other cancers, including those that have copy number gains in 20q13. Accordingly, the invention provides methods of identifying inhibitors of PFDN-4 and methods of treating cancer, e.g., by inhibiting the expression and/or activity of PFDN-4. The invention also provides methods to detect cancer or a propensity to develop cancer, to monitor the efficacy of a cancer treatment, and/or of using the sequence for prognostic applications.

Thus, in one aspect, the invention provides a method of identifying a modulator of expression of a cancer-associated polypeptide, the method comprising the steps of: (i) contacting a cell that expresses PFDN-4, e.g., SEQ ID NO:2, with a candidate modulator; and (ii) determining the level of expression of PFDN-4. In some embodiments, the modulator is a nucleic acid such as a ribozyme, antisense nucleic acid, or an siRNA The invention also provides a method for identifying a compound that modulates a cancer-associated polypeptide, the method comprising the steps of: (i) contacting the compound with a PFDN-4 polypeptide, (e.g., SEQ ID NO:2); and (ii) determining the functional effect of the compound upon the polypeptide. The compounds can be, e.g., a small organic molecule or an antibody.

In another aspect, the invention provides a method of inhibiting proliferation of a cancer cell that overexpresses a PFDN-4 polypeptide, e.g., a PFDN-4 having the amino acid sequence of SEQ ID NO:2, the method comprising the step of contacting the cancer cell with a therapeutically effective amount of an inhibitor of the PFDN-4 polypeptide. In some embodiments, the cell has an amplification of 20q13. An inhibitor can be, e.g., a small organic molecule, an antibody, an antisense molecule, a ribozyme, or an siRNA molecule.

In another aspect, the invention provides a method of detecting cancer in a biological sample from a patient, the method comprising: contacting the sample with a polynucleotide that selectively hybridizes to a nucleic acid sequence encoding a PFDN-4 polypeptide, e.g., a PFDN-4 polypeptide having the amino acid sequence of SEQ ID NO:2; and determining an increase in the level of the nucleic acid sequence, relative to normal, thereby detecting the presence of cancer in the patient. In some embodiments, the cancer comprises cells that have an amplification in the chromosomal region 20q13. The method can be used to detect many different cancers, including ovarian cancer, breast cancer, cervical cancer, gastric adenocarcinomas, uroepithelial tumors, and islet tumors.

In some embodiments, the detecting step comprises detecting an increase in copy number of the gene that encodes the PFDN-4 polypeptide. In other embodiments, the detecting step comprises detecting an mRNA that encodes PFDN-4.

In some applications of the methods, the patient is suspected of having cancer. In other applications, the patient is undergoing a therapeutic regimen to treat cancer.

The invention also provides a method of detecting cancer in a biological sample from a patient, the method comprising: detecting an increase in the level of a PFDN-4 polypeptide, e.g., a PFDN-4 polypeptide having the amino acid sequence of SEQ ID NO:2, relative to normal, thereby detecting the presence of cancer in the patient. Typically, the level of the polypeptide is determining using an immunoassay. In other embodiments, PFDN-4 activity is used to determine whether an increase in PFDN-4 levels is present.

The invention also provides a method of monitoring the efficacy of a therapeutic treatment of cancer, the method comprising the steps of: (i) providing a biological sample from a patient undergoing the therapeutic treatment; and (ii) detecting the level of: a PFDN-4 polypeptide, e.g., a PFDN-4 polypeptide having an amino acid sequence of SEQ ID NO:2, or of a nucleic acid that encodes the polypeptide, in the biological sample compared to a level in a biological sample from the patient prior to, or earlier in, the therapeutic treatment, thereby monitoring the efficacy of the therapy.

BRIEF DESCRIPTION OF THE DRAWINGS

FIG. 4 provides exemplary data showing the correlation between PFDN-4 expression levels and DNA copy number in 19 human breast cancer cell lines. PFDN-4 expression levels were determined by qRT-PCR and DNA copy number in 20q13.2 genomic region by array Comparative Genome Hybridization (aCGH). Each spot represents a different cell line. The Pearsons correlation coefficient between expression and copy number is 0.85 (where 0.3 is the significance threshold).

DETAILED DESCRIPTION OF THE INVENTION

Introduction

Figure 1:
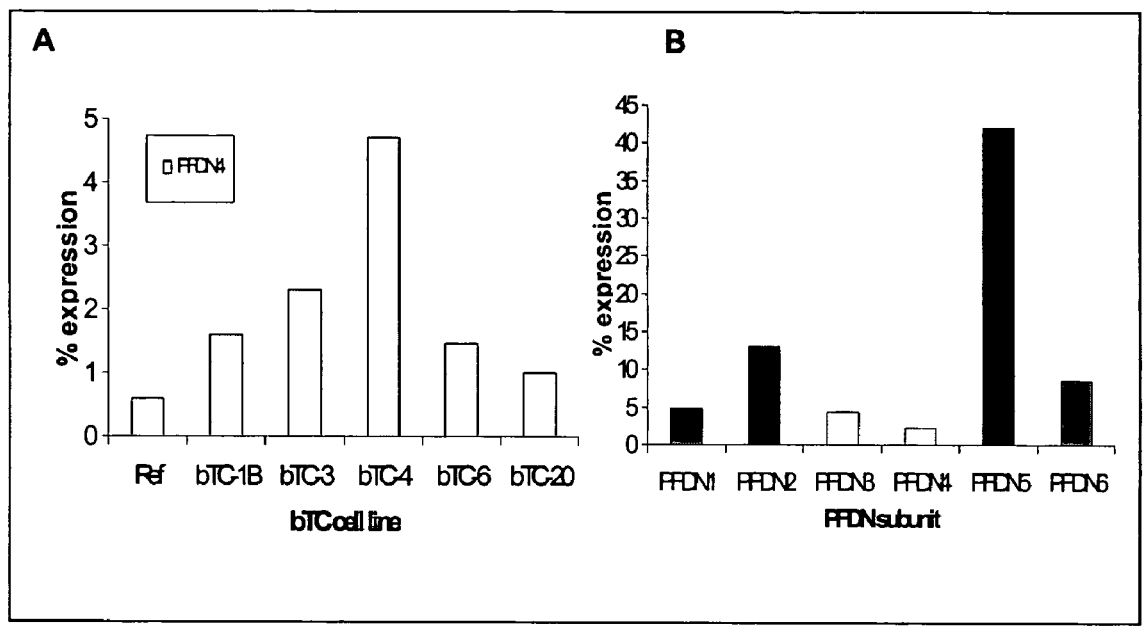
FIG. 1 provides exemplary data showing prefoldin subunit expression levels in different βTC cell lines A, PFDN-4 characterization βTC cell lines derived from primary tumors (1B, 3, 4, 6, and 20) and Universal Mouse Reference RNA as positive control. B, Expression levels of six Prefoldin component genes by qRT-PCR in βTC3, a cee line lacking amplification in mChr_2.

The present invention provides methods, reagents, and kits for diagnosing cancer, for prognostic uses, and for treating cancer. The invention is based upon the discovery that PFDN-4 polynucleotide and polypeptides are amplified and/or overexpressed in cancer cells and play a role in tumor growth. Cancers that can be detected using PFDN-4 reagents and/or treated by inhibiting PFDN-4 expression include breast cancer, ovarian cancer, cervical cancer, gastric adenocarcinomas, uroepithelial tumors, uterus adenoma, mesothelioma, follicular lymphoma, lung adenocarcinoma, lung squamous carcinoma, renal carcinoma, pancreatic adenoma, medulloblastoma, small cell lung cancer, acute lymphocytic leukemia (B-cell), acute lymphocytic leukemia (T-cell), and acute myelomonocytic leukemia.

PFDN-4 plays a role in protein folding as part of the prefoldin complex. Prefoldin polynucleotide and polypeptides sequences are known. For example, human PFDN-4 polynucleotide sequences are available under the reference sequences NM_002623.2, BC010953.1, and U41816.1. An exemplary human polypeptide sequence is available under the accession number Q9NQP4. The OMIM reference number for human PFDN-4 is 604898 and the UniGene number is Hs.91161.

The ability to detect cancer cells by virtue of detecting an increased level of a PFDN-4 nucleic acid or polypeptide sequence is useful for any of a large number of applications. For example, an increased level of polynucleotides or proteins in cells of patient can be used, alone or in combination with other diagnostic methods, to diagnose cancer in the patient or to determine the propensity of a patient to develop cancer. The detection of PFDN-4 sequences can also be used to monitor the efficacy of a cancer treatment. For example, the level of a PFDN-4 polypeptide or polynucleotide after an anti-cancer treatment is compared to the level before the treatment. A decrease in the level of the PFDN-4 polypeptide or polynucleotide after the treatment indicates efficacious treatment.

An increased level or diagnostic presence of PFDN-4 can also be used to influence the choice of anti-cancer treatment, where, for example, the increased level of PFDN-4 directly correlates with the aggressiveness of the cancer and accordingly, the selection of anti-cancer therapy.

In addition, the ability to detect cancer cells can be useful to monitor the number or location of cancer cells in a patient, in vivo or in vitro, for example, to monitor the progression of the cancer over time. In addition, the level of PFDN-4 can be statistically correlated with the efficacy of particular anti-cancer therapies or with observed prognostic outcomes, thereby allowing the development of databases based on which a statistically-based prognosis, or a selection of the most efficacious treatment, can be made in view of a particular level or diagnostic presence of PFDN-4.

The present invention also provides methods of identifying inhibitors of PFDN-4 and methods for treating cancer by inhibiting PFDN-4 expression or activity. In certain embodiments, the proliferation is inhibited in a cancer cell that has an increase in copy number of PFDN-4 and overexpresses PFDN-4. The proliferation is decreased by, for example, contacting the cell with an inhibitor of PFDN-4 transcription or translation, or an inhibitor of the activity of PFDN-4. Such inhibitors include, but are not limited to, small molecule inhibitors, siRNAs, antisense polynucleotides, ribozymes, and dominant negative PFDN-4 polynucleotides or polypeptides, and antibodies.

Definitions

The term "PFDN-4" refers to nucleic acid and polypeptide polymorphic variants, alleles, mutants, and interspecies homologues that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity to PFDN-4 sequence of SEQ ID NO:2 or over a region of at least about 20, 50, 75, 100, or 125 or more amino acids of SEQ ID NO:2; (2) bind to antibodies, e.g., polyclonal antibodies, raised against an immunogen comprising an amino acid sequence of SEQ ID NO:2, or conservatively modified variants thereof; (3) specifically hybridize under stringent hybridization conditions to a PFDN-4 nucleic acid sequence of SEQ ID NO:1 or conservatively modified variants thereof; or (4) or have a nucleic acid sequence that has greater than about 90%, preferably greater than about 96%, 97%, 98%, 99%, or higher nucleotide sequence identity, preferably over a region of over a region of at least about 30, 50, 100, 200, or 300 or more nucleotides, to SEQ ID NO:1; or (5) have at least 25, often 50, 75, or 100, 110, 120, or more contiguous amino acid of SEQ ID NO:2; or at least 25, often 50, 75, 100, 150, 200, 250, 300, or 350 or more contiguous nucleotides of SEQ ID NO:1. A PDN-4 polynucleotide or polypeptide sequence is typically from a human, but may be from other mammals, but not limited to, a non-human primate, a rodent, e.g.; a mouse, rat, or hamster; a cow, a pig, a horse, a sheep, or other mammal. A "PFDN-4" polypeptide and a "PFDN-4" polynucleotide include both naturally occurring or recombinant forms.

A "full length" PFDN-4 protein or nucleic acid refers to a PFDN-4 polypeptide or polynucleotide sequence, or a variant thereof, that contains all of the elements normally contained in one or more naturally occurring, wild type PFDN-4 polynucleotide or polypeptide sequences. The "full length" may be prior to, or after, various stages of post-translation processing or splicing, including alternative splicing.

"Biological sample" as used herein is a sample of biological tissue or fluid that contains nucleic acids or polypeptides, e.g., of a PFDN-4 protein, polynucleotide or transcript. Such samples are typically from humans, but include tissues isolated from non-human primates, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues.

"Providing a biological sample" means to obtain a biological sample for use in methods described in this invention.

Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, will be particularly useful.

The "level of PFDN-4 mRNA" in a biological sample refers to the amount of mRNA transcribed from an PFDN-4 gene that is present in a cell or a biological sample. The mRNA generally encodes a functional PFDN-4 protein, although mutations may be present that alter or eliminate the function of the encoded protein. A "level of PFDN-4 mRNA" need not be quantified, but can simply be detected, e.g., a subjective, visual detection by a human, with or without comparison to a level from a control sample or a level expected of a control sample.

The "level of PFDN-4 protein or polypeptide" in a biological sample refers to the amount of polypeptide translated from PFDN-4 mRNA that is present in a cell or biological sample. The polypeptide may or may not have PFDN-4 protein activity. A "level of PFDN-4 protein" need not be quantified, but can simply be detected, e.g., a subjective, visual detection by a human, with or without comparison to a level from a control sample or a level expected of a control sample.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915)). For the purposes of this invention, the BLAST2.0 algorithm is used with the default parameters and the filter off.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor & Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the non-covalent association of independent tertiary units.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the PFDN-4 nucleic acids, proteins and antibodies at any position. Any method known in the art for conjugating the antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The phrase "functional effects" in the context of assays for testing compounds that modulate activity of a PFDN-4 protein includes the determination of a parameter that is indirectly or directly under the influence of the PFDN-4 cancer protein or nucleic acid, e.g., a functional, physical, or chemical effect, such as the ability to decrease tumorigenesis. It includes protein-protein interaction activity; cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo, including measurement of tumor growth and tumor "take" in a model system; mRNA and protein expression in cells, including those undergoing metastasis, and other characteristics of cancer cells. "Functional effects" include in vitro, in vivo, and ex vivo activities.

By "determining the functional effect" is meant assaying for a compound that increases or decreases a parameter that is indirectly or directly under the influence of a PFDN-4 protein sequence, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the PFDN-4 protein; measuring binding activity or binding assays, e.g. binding to antibodies or other ligands, and measuring cellular proliferation. Determination of the functional effect of a compound on tumorigenesis can be performed using exemplary assays disclosed above. The functional effects can be evaluated by many means known to those skilled in the art, e.g., microscopy for quantitative or qualitative measures of alterations in morphological features, measurement of changes in RNA or protein levels for PFDN-4 sequences, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays.

"Inhibitors" or "modulators" of PFDN-4 polynucleotide and polypeptide sequences are used to refer to inhibitory molecules or compounds identified using in vitro and in vivo assays of PFDN-4 polynucleotide and polypeptide sequences. Inhibitors are compounds that, e.g., bind to, partially or totally block activity, decrease, prevent, delay activation, inactivate, desensitize, or down regulate the activity or expression of PFDN-4 proteins, e.g., antagonists. Inhibitors include siRNA or antisense RNA, genetically modified versions of PFDN-4 proteins, e.g., versions with altered activity, as well as naturally occurring and synthetic PFDN antagonists, antibodies, small chemical molecules and the like. Such assays for inhibitors and activators include, e.g., expressing the PFDN-4 protein in vitro, in cells, or cell membranes, applying putative modulator compounds, and then determining the functional effects on activity, as described above.

Samples or assays comprising PFDN-4 proteins that are treated with a potential inhibitor are compared to control samples without the inhibitor, to examine the extent of inhibition. Control samples (untreated with inhibitors) are assigned a relative protein activity value of 100%. Inhibition of a PFDN-4 polypeptide is achieved when the activity value relative to the control is about 80%, preferably 50%, more preferably 25-0%.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* ($3^{rd}$ ed. 1994)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Identification of PFDN-4 Sequences in a Sample from a Patient

In one aspect of the invention, the expression levels of PFDN-4 are determined in different patient samples for which diagnostic or prognostic information is desired. That is, normal tissue may be distinguished from cancerous or metastatic cancerous tissue, e.g., cancerous or metastatic ovarian or breast tissuet; or cancer tissue or metastatic cancerous tissue can be compared with corresponding tissue samples from other patients, e.g., surviving cancer patients.

General Recombinant DNA Methods

This invention relies on routine techniques in the field of recombinant genetics for the preparation of PFDN-4 for use in the invention and for methods of detecting PFDN-4. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999). Methods that are used to produce PFDN-4 for use in the invention may also be employed to produce other polypeptides, e.g., candidate modulators, for use in the invention. For nucleic acids, sizes are given in either kilobases (kb) or base pairs (bp). For proteins, sizes are given in kilodaltons (kDa) or amino acid residue numbers.

Methods for the Isolation and Expression of PFDN-4 Nucleotide Sequences

In general, the nucleic acid sequences encoding PFDN-4 and related nucleic acid sequence homologs are cloned from cDNA and genomic DNA libraries by hybridization with a probe, or isolated using amplification techniques with oligonucleotide primers. For example, sequences are typically isolated from mammalian nucleic acid (genomic or cDNA) libraries by hybridizing with a nucleic acid probe, the sequence of which can be derived from SEQ ID NOS:1. Amplification techniques using primers can also be used to amplify and isolate nucleic acids from DNA or RNA (see, e.g., section "detection of polynucleotides", below). Suitable primers for amplification of specific sequences can be designed using principles well known in the art (see, e.g., Dieffenbach & Dveksler, *PCR Primer: A Laboratory Manual* (1995)). These primers can be used, e.g., to amplify either the full length sequence or a probe that is then used to identify PFDN-4 polynucleotides.

Nucleic acids encoding PFDN-4 can also be isolated from expression libraries using antibodies as probes. Such polyclonal or monoclonal antibodies can be raised using the sequence of SEQ ID NOs:2.

Synthetic oligonucleotides can also be used to construct PFDN-4 genes for use as probes or for expression of protein. This method is performed using a series of overlapping oligonucleotides, usually 40-120 bp in length, representing both the sense and nonsense strands of the gene. These DNA fragments are then annealed, ligated and cloned. Alternatively, amplification techniques can be used with precise primers to amplify a specific subsequence of the nucleic acid. The specific subsequence is then ligated into an expression vector.

To obtain high level expression of a cloned gene or nucleic acid, such as cDNAs encoding PFDN-4, one typically subdlones a PFDN-4 nucleic acid into an expression vector that contains a strong promoter to direct transcription, a transcription/translation terminator, and if for a nucleic acid encoding a protein, a ribosome binding site for translational initiation. Additional elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences.

Suitable bacterial and eukaryotic expression systems promoters are well known in the art and described, e.g., in Sambrook & Russell, supra, Ausubel et al, supra. Bacterial expression systems for expressing the PFDN-4 protein include e.g., *E. coli, Bacillus* sp., and *Salmonella*. Eukaryotic expression systems include those for expressing sequences in mamralian cells, yeast, and insect cells. In one embodiment, the eukaryotic expression vector is a viral vector, e.g., an adenoviral vector, an adeno-associated vector, or a retroviral vector. Kits for prokaryotic and eukaryotic expression systems are commercially available.

Standard transfection methods are used to produce bacterial, mammalian, yeast or insect cell lines that express large quantities of PFDN-4 protein, which are then purified using standard techniques (see, e.g., Scopes, *Protein Purification: Principles and Practice* (1982); U.S. Pat. No. 4,673,641; Ausubel et al., supra; and Sambrook et al., supra *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Detection of Polynucleotides

The invention provides methods for detecting PFDN-4 polynucleotide and polypeptide sequences, e.g., for the diagnosis and prognosis of cancer. Typically, the level of a PFDN-4 polynucleotide or polypeptide will be detected in a biological sample. As noted above, a "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a saliva sample, or a nipple discharge.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

Detection of Copy Number

In one embodiment, diagnostic and prognostic detection of PFDN-4 in cancer is evaluated by determining the copy number of PFDN-4, i.e., the number of DNA sequences in a cell encoding PFDN-4. Methods of evaluating the copy number of a particular gene are well known to those of skill in the art, and include, inter alia, hybridization and amplification based assays.

Hybridization-based Assays

Any of a number of hybridization based assays can be used to detect the copy number of PFDN-4 in the cells of a biological sample. One such method is by Southern blot. In a Southern blot, genomic DNA is typically fragmented, separated electrophoretically, transferred to a membrane, and subsequently hybridized to a cancer-associated polynucleotide-specific probe. Comparison of the intensity of the hybridization signal from the probe for the target region with a signal from a control probe for a region of normal genomic DNA (e.g., a nonamplified portion of the same or related cell, tissue, organ, etc.) provides an estimate of the relative copy number of the cancer-associated gene. Southern blot methodology is well known in the art and is described, e.g., in Ausubel et al., or Sambrook et al., supra.

An alternative means for determining the copy number of PFDN-4 in a sample is by in situ hybridization, e.g., fluorescence in situ hybridization, or FISH. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In numerous embodiments, "comparative probe" methods, such as comparative genomic hybridization (CGH), are used to detect PFDN-4 gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in an array. Differences in the ratio of the signals from the two labels, e.g., due to gene amplification in the test collection, is detected and the ratio provides a measure of the PFDN-4 gene copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: *In Situ Hybridization Protocols*, Choo, ed., Humana Press, Totowa, N.J. (1994), etc.

Amplification-based Assays

In another embodiment, amplification-based assays are used to measure the copy number of PFDN-4. In such an assay, the PFDN-4 nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the cancer-associated gene. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). The known nucleic acid sequences for PFDN-4 (see, e.g., SEQ ID NO:1) is sufficient to enable one of skill to routinely select primers to amplify any portion of the gene. Suitable primers for amplification of specific sequences can be designed using principles well known in the art (see, e.g., Dieffenbach & Dveksler, *PCR Primer: A Laboratory Manual* (1995))

In preferred embodiments, a TaqMan® quantitative RT-PCR assay is used to quantify the cancer-associated polynucleotides. TaqMan® quantitative RT-PCR assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq®, results in the cleavage of the fluorogenic oligonucleotide probe. This cleavage separates the 5' fluorescent dye and the 3' quenching agent, thereby resulting in an increase in fluorescence as a function of amplification.

Other suitable amplification methods include, but are not limited to, ligase chain reaction (LCR) (see, Wu and Wallace (1989) *Genomics* 4: 560, Landegren et al. (1988) *Science* 241: 1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

Detection of mRNA Expression

Direct Hybridization-based Assays

Methods of detecting and/or quantifying the level of PFDN-4 gene transcripts (mRNA or cDNA made therefrom) using nucleic acid hybridization techniques are known to those of skill in the art. For example, expression levels of PFDN-4 can also be analyzed by techniques known in the art, e.g., dot blotting, in situ hybridization, RNase protection, probing DNA microarrays, and the like. In one embodiment, high density oligonucleotide analysis technology (e.g., GeneChip®™ microchip array) is used to identify PFDN-4 sequences.

Amplification-based Assays

In another embodiment, a PFDN-4 transcript is detected using amplification-based methods (e.g., RT-PCR). RT-PCR methods are well known to those of skill (see, e.g., Ausubel et al., supra). Preferably, quantitative RT-PCR, e.g., a TaqMan® assay, is used, thereby allowing the comparison of the level of mRNA in a sample with a control sample or value.

Detection of PFDN-4 Polypeptide Sequences

Altered PFDN-4 expression or activity can also be detected by detecting levels of PFDN-4 protein or activity. For example, detection of PfDN-4 protein activity or expression can be used for diagnostic purposes or in screening assays. In some embodiments, PFDN-4 level is conveniently determined using immunological assays to detect the level of PFDN-4 polypeptides. The following section discusses immunological detection of PFDN-4. The section also relates to generation and engineering of therapeutic antibodies.

Immunological Detection PFDN-4

Antibodies can also be used to detect PFDN-4 or can be assessed in the methods of the invention for the ability to inhibit PFDN-4. PFDN-4 or a fragment thereof may be used to produce antibodies specifically reactive with PFDN-4. For example, a recombinant PFDN-4 or an antigenic fragment thereof, is isolated as described herein. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then used to generate antibodies.

A general overview of the applicable technology can be found in Harlow & Lane, *Antibodies: A Laboratory Manual* (1988) and Harlow & Lane, *Using Antibodies* (1999). Methods of producing polyclonal and monoclonal antibodies that react specifically with PFDN-4 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341: 544-546 (1989)). Such antibodies can be used for diagnostic or prognostic applications, e.g., in the detection of cancer, e.g., ovarian, breast cancer, cervical cancer, pancreatic islet cancer, or for other cancers that exhibit increased expression or activity of PFDN-4.

Typically, polyclonal antisera with a titer of $10^4$ or greater are selected and tested for their cross reactivity against non-PFDN-4 proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

In some embodiments, a PFDN-4 antibody may be used for therapeutic applications. For example, such an antibody may be conjugated to a protein that facilitates entry into the cell. In one case, the antibody enters the cell by endocytosis. In another embodiment, a nucleic acid encoding the antibody is administered to the individual or cell.

In one embodiment, the antibodies to the PFDN-4 protein are capable of reducing or eliminating a biological function of PFDN-4 as is described below. That is, the addition of anti-PFDN-4 antibodies (either polyclonal or preferably monoclonal) to cancer tissue (or a cell population containing cancerous cells) may reduce or eliminate the cancer. Generally, at least a 25% decrease in activity, growth, size or the like is preferred, with at least about 50% being particularly preferred and about a 95-100% decrease being especially preferred.

Often, the antibodies to the PFDN-4 proteins for therapeutic applications are humanized antibodies (e.g., Xenerex Biosciences, Mederex, Inc., Abgenix, Inc., Protein Design Labs, Inc.) Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332: 323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633, 425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

Once PFDN-4-specific antibodies are available, binding interactions with PFDN-4 can be detected by a variety of immunoassay methods. PFDN-4 can be detected and/or quantified using any of a number of well recognized immunological binding assays (see, e.g., U.S. Pat. Nos. 4,366,241; 4,376,110; 4,517,288; and 4,837,168). For areview of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case PFDN-4 or antigenic subsequence thereof). The immunoassays can be performed in any of several configurations, which are reviewed extensively in *Enzyme Immunoassay* (Maggio, ed., 1980); and Harlow & Lane, supra.

Immunoassays also often use a labeling agent to specifically bind to and label the complex formed by the antibody and antigen. The labeling agent may itself be one of the moieties comprising the antibody/antigen complex. Thus, the labeling agent may be a labeled PFDN-4 polypeptide or a labeled anti-PFDN-4 antibody. Alternatively, the labeling agent may be a third moiety, such as a secondary antibody, that specifically binds to the antibody/ antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of PFDN-4 present in the sample is measured indirectly by measuring the amount of a known, added (exogenous) PFDN-4 displaced (competed away) from an anti-PFDN-4 antibody by the unknown PFDN-4 present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent compounds (e.g., fluorescein isothiocyanate, Texas red, rhodamine, fluorescein, and the like), radiolabels, enzymes (e.g., horse radish peroxidase, alkaline phosphatase and others commonly used in an ELISA), streptavidin/biotin, and calorimetric labels such as colloidal gold or colored glass or plastic beads (e.g., polystyrene, polypropylene, latex, etc.). Chemiluminescent compounds may also be used. For a review of various labeling or signal producing systems that may be used, see U.S. Pat. No. 4,391,904.

Detection of Activity

As appreciated by one of skill in the art, PFDN-4 activity can be detected to evaluate expression levels or for identifying modulators of activity. The activity can be assessed using a variety of in vitro and in vivo assays to determine functional, chemical, and physical effects, e.g., measuring protein-protein interactions, measuring apoptosis, measuring transcription levels, measuring indicators of transformation, e.g., growth in soft agar, change in cell phenotype, ability to modify tumorigenesis, and the like. For example, PFDN-4 is a member of the prefoldin complex. Thus, in some embodiments, PFDN-4 activity can be assessed by monitoring prefoldin assembly and/or monitoring the ability of PFDN-4 to interact with other components of prefoldin.

In other embodiments, as noted above, the ability of a test compound to modulate PFDN-4 is tested by examining markers of cellular transformation or apoptosis. In these embodiments, a candidate inhibitor is examined for the ability to inhibit transformation-associated phenotypic changes of cells and/or apoptosis. Such tests may be performed in vitro or in vivo. For example, a candidate compound may be tested for the ability to counteract PFDN-4-associated decreases in apoptosis. Alternatively, a candidate compound may be tested for the ability to decreased the enhanced tumor "take" rates associated with PFDN-4 overexpression using an animal model, such as a mouse model of tumorigenesis (see, e.g., the Examples section).

The PFDN-4 for the assay is often selected from a polypeptide having a sequence of SEQ ID NO:2, or conservatively modified variants thereof. Alternatively, the PFDN-4 will be derived from a eukaryote and include an amino acid subsequence having amino acid sequence identity to SEQ ID NO:2. Generally, the amino acid sequence identity will be at least 70%, optionally at least 80%, or 90-95%. The PFDN-4 typically comprises at least 10 contiguous amino acids, often at least 20, 50, or 100 contiguous amino acids of SEQ ID NO:2. Optionally, the polypeptide of the assays will comprise or consist of a domain of PFDN-4, such as a subunit association domain, active site, and the like. Either a PFDN-4 or a domain thereof can be covalently linked to a heterologous protein to create a chimeric protein used in the assays described herein.

Activity assays of the invention are used to identify modulators that can be used as therapeutic agents, e.g., antibodies to PFDN-4 and antagonists of PFDN-4 activity Modulators of PFDN-4 activity are tested using PFDN-4 polypeptides as described above, either recombinant or naturally occurring. The protein can be isolated, expressed in a cell, expressed in tissue or in an animal, either recombinant or naturally occurring. For example, transformed cells can be used. Modulation is tested using one of the in vitro or in vivo assays described herein. Activity can also be examined in vitro with soluble or solid state reactions, using a PFDN-4 fragment that binds to another protein, e.g, another component of the prefoldin complex.

In another embodiment, mRNA and/or protein expression levels can be measured to assess the effects of a test compound on PFDN-4. A host cell expressing PFDN-4 is contacted with a test compound for a sufficient time to effect any interactions, and then the level of mRNA or protein is measured. The amount of time to effect such interactions may be empirically determined, such as by running a time course and measuring the level of expression as a function of time. The amount of expression may be measured by using any method known to those of skill in the art to be suitable. For example, mRNA expression may be detected using northern blots or polypeptide levels may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. In such an assay, the reporter gene is typically under control of a regulatory region e.g., a promoter, from the PFDN-4 gene.

The amount of expression is then compared to the amount of expression in the absence of the test compound. A substantially identical cell may be derived from the same cells from which the recombinant cell was prepared but which had not been modified by introduction of heterologous DNA. A difference in the amount of expression indicates that the test compound has in some manner altered PFDN-4 levels.

In assays to identify PFDN-4 inhibitors, samples that are treated with a potential inhibitor are compared to control samples to determine the extent of modulation. Control samples (untreated with candidate inhibitors) are assigned a relative activity value of 100. Inhibition of PFDN-4 is achieved when the activity value relative to the control is about 80%, optionally 50%, optionally 25-0%.

Candidate Compounds

The compounds tested as inhibitors of PFDN-4 can be any small chemical compound, or a biological entity, e.g., a macromolecule such as a protein, sugar, nucleic acid or lipid. Alternatively, modulators can be genetically altered versions of PFDN-4. Typically, test compounds will be small chemical molecules and peptides or antibodies.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a LogP over 5 (or MLogP over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

Essentially any chemical compound can be used as a potential modulator or ligand in the assays of the invention. Most often, compounds can be dissolved in aqueous or organic (especially DMSO-based) solutions. The assays are designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Solid State and Soluble High Throughput Assays

In one embodiment the invention provides soluble assays using molecules such as a domain, e.g., a binding domain, a subunit association region, etc.; a domain that is covalently linked to a heterologous protein to create a chimeric molecule; a PFDN-4; or a cell or tissue expressing a PFDN-4, either naturally occurring or recombinant. In another embodiment, the invention provides solid phase based in vitro assays in a high throughput format, where the domain, chimeric molecule, PFDN-4, or cell or tissue expressing PFDN-4 is attached to a solid phase substrate. In high throughput screening assays, it is possible to screen up to several thousand different modulators or ligands in a single day.

The molecule of interest can be bound to the solid state component, directly or indirectly, via covalent or non covalent linkage e.g., via a tag. The tag can be any of a variety of components. In general, a molecule that binds the tag (a tag binder) is fixed to a solid support, and the tagged molecule of interest (e.g., the prefoldin complex member of interest) is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and are appropriate tag binders; see, SIGMA Immunochemicals 1998 catalogue SIGMA, St. Louis Mo.). Similarly, any haptenic or antigenic compound can be used in combination with an appropriate antibody to form a tag/tag binder pair. Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:3). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Computer-based Assays

Yet another assay for compounds that modulate PFDN-4 activity involves computer assisted drug design, in which a computer system is used to generate a three-dimensional structure of PFDN-4 based on the structural information encoded by the amino acid sequence. The input amino acid sequence interacts directly and actively with a pre-established algorithm in a computer program to yield secondary, tertiary, and quaternary structural models of the protein. The models of the protein structure are then examined, for example, to identify the regions that have the ability to bind other members of the prefoldin complex. These regions are then used to identify various compounds that inhibit PFDN-4 activity.

The three-dimensional structural model of the protein is generated by entering protein amino acid sequences of at least 10 amino acid residues or corresponding nucleic acid sequences encoding a PFDN-4 polypeptide into the computer system. The amino acid sequence may comprise SEQ ID NO: 2. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble and its cellular location, e.g., cytoplasmic. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of PFDN-4 to identify ligands that bind to the PFDN-4. Binding affinity between the protein and ligands is determined using energy terms to determine which ligands have an enhanced probability of binding to the protein.

Expression Assays

Certain screening methods involve screening for a compound that modulates the expression of PFDN-4. Such methods generally involve conducting cell-based assays in which test compounds are contacted with one or more cells expressing a PFDN-4 and then detecting a decrease in expression (either transcript or translation product). Such assays are often performed with cells that overexpress PFDN-4.

Expression can be detected in a number of different ways. As described herein, the expression levels of the protein in a cell can be determined by probing the mRNA expressed in a cell with a probe that specifically hybridizes with a PFDN-4 transcript (or complementary nucleic acid derived therefrom). Alternatively, protein can be detected using immunological methods in which a cell lysate is probed with antibodies that specifically bind to the protein.

Other cell-based assays are reporter assays conducted with cells that do not express the protein. Often, these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase), luciferase, β-galactosidase and alkaline phosphatase.

In these assays, cells harboring the reporter construct are contacted with a test compound. A test compound that inhibits the activity of the promoter, e.g., by binding to it or triggering a cascade that produces a molecule that decreases the promoter-induced expression of the detectable reporter can be detected by comparison to control cells that have not been treated with the inhibitor. Certain other reporter assays are conducted with cells that harbor a heterologous construct that includes a transcriptional control element that activates expression of PFDN-4 and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

In another embodiment, PFDN-4are used to generate animal models of cancer. For example, a transgenic animals can be generated that overexpresses PFDN-4. Depending on the desired expression level, promoters of various strengths can be employed to express the transgene. Also, the number of copies of the integrated transgene can be determined and compared for a determination of the expression level of the transgene. Animals generated by such methods can be used for screening for inhibitors to treat cancer. mo Nucleic Acid Inhibitors Screening assays of the invention often evaluate nucleic acid molecules as potential inhibitors. For example, ribozymes, antisense RNA and/or small interfering RNA (siRNA) molecules can be screened for the ability to decrease PFDN-4 levels.

I some embodiments, siRNA molecules designed to target PFDN-4 RNA are screened. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, *Nature* 411:428-29 (2001); Elbahir et al., *Nature* 411:494-98 (2001); and Fire et al., *Nature* 391:806-11 (1998), where methods of making interfering RNA also are discussed. The siRNAs based upon the PFDN-4 sequences disclosed herein are less than 100 base pairs, typically 30 bps or shorter, and are made by approaches known in the art. Exemplary siRNAs according to the invention could have up to 29 bps, 25 bps, 22 bps, 21 bps, 20 bps, 15 bps, 10 bps, 5 bps or any integer thereabout or therebetween.

The siRNA can comprise two complementary molecules, or can be constructed such that a single transcript has both the sense and complementary antisense sequences from the target gene, e.g., a hairpin.

Methods for designing double stranded RNA to inhibit gene expression in a target cell are known (see, e.g., U.S. Pat. No. 6,506,559; Elbashir et al. *Methods* 26:199-213, 2002; Chalk et al., *Biochem. Biophysy. Res. Comm* 319:264-274, 2004; Cui et al. *Computer Method and Programs in Biomedicine* 75:67-73, 2004, Wang et al., Bioinformatics 20:1818-1820, 2004). For example, design of siRNAs (including hairpins) typically follow known thermodynamic rules (see, e.g., Schwarz, et al., *Cell* 115:199-208, 2003; Reynolds et al., *Nat Biotechnol*. 22:326-30, 2004; Khvorova, et al., *Cell* 115:209-16, 2003). Many computer programs are available for selecting regions of PFDN-4 that are suitable target sites. These include programs available through commercial sources such as Ambion, Dharmacon, Promega, Invitrogen, Ziagen, and GenScript as well as noncommercial sources such as EMBOSS, The Wistar Institute, Whitehead Institute, and others.

For example, design can be based on the following considerations. Typically shorter sequences, i.e., less than about 30 nucleotides are selected. The coding region of the mRNA is usually targeted. The search for an appropriate target sequence optionally begins 50-100 nucleotides downstream of the start codon, as untranslated region binding proteins and/or translation initiation complexes may interfere with the binding of the siRNP endonuclease complex. Some algorithms, e.g., based on the work of Elbashir et al., supra, search for a 23-nt sequence motif AA(N19)TT (SEQ ID NO:4) (N, any nucleotide) and select hits with approx. 50% G/C-content (30% to 70% has also worked in for them). If no suitable sequences are found, the search is extended using the motif NA(N21). The sequence of the sense siRNA corresponds to (N19)TT or N21 (position 3 to 23 of the 23-nt motif), respectively. In the latter case, the 3' end of the sense siRNA is converted to TT.

Other algorithisms preferentially select siRNAs corresponding to the target motif NAR(N17)YNN, where R is purine (A, G) and Y is pyrimidine (C, U). The respective 21-nt sense and antisense siRNAs therefore begin with a purine nucleotide and can also be expressed from pol III expression vectors without a change in targeting site; expression of RNAs from pol III promoters is only efficient when the first transcribed nucleotide is a purine.

Other nucleic acids, e.g., ribozymes, antisense, can also be designed based on known principles. For example, Sfold (see, e.g, Ding, et al., *Nucleic Acids Res*. 32 Web Server issue, W135-W141, Ding & Lawrence, *Nucl. Acids Res*. 31: 7280, 7301, 2003; and Ding & Lawrence *Nucl. Acids Res*. 20:1034-1046, 2001) provides programs relating to designing ribozymes and antisense, as well as siRNAs.

Disease Treatment and Diagnosis/Prognosis

PFDN-4 nucleic acid and polypeptide sequences can be used for diagnosis or prognosis of cancer in a patient. For example, the sequence, level, or activity of PFDN-4 in a patient can be determined, wherein an alteration, e.g., an increase in the level of expression or activity of PFDN-4, or the detection of an increase in copy number or mutations in the PFDN-4, indicates the presence or the likelihood of cancer.

Often, such methods will be used in conjunction with additional diagnostic methods, e.g., detection of other cancer indicators, e.g., cell morphology, and the like. In other embodiments, a tissue sample known to contain cancerous cells, e.g., from a tumor, will be analyzed for PFDN-4 levels to determine information about the cancer, e.g., the efficacy of certain treatments, the survival expectancy In some embodiments, the level of PFDN-4 can be used to determine the prognosis of a patient with cancer. For example, if cancer is detected using a technique other than by detecting PFDN-4, e.g., tissue biopsy, then the presence or absence of PFDN-4 can be used to determine the prognosis for the patient, i.e., an elevated level of PFDN-4 will typically indicate a reduced survival expectancy in the patient compared to in a patient with cancer but with a normal level of PFDN-4. As used herein, "survival expectancy" refers to a prediction regarding the severity, duration, or progress of a disease, condition, or any symptom thereof. In a preferred embodiment, an increased level, a diagnostic presence, or a quantified level, of PFDN-4 is statistically correlated with the observed progress of a disease, condition, or symptom in a large number of patients, thereby providing a database wherefrom a statistically-based prognosis can be made. For example, in a particular type of patient, a human of a particular age, gender, medical condition, medical history, etc., a detection of a level of PFDN-4 that is, e.g., 2 fold higher than a control level may indicate, e.g., a 10% reduced survival expectancy in the human compared to in a similar human with a normal level of PFDN-4, based on a previous study of the level of PFDN-4 in a large number of similar patients whose disease progression was observed and recorded.

The methods of the present invention can be used to determine the optimal course of treatment in a patient with cancer. For example, the presence of an elevated level of PFDN-4 can indicate a reduced survival expectancy of a patient with cancer, thereby indicating a more aggressive treatment for the patient In addition, a correlation can be readily established between levels of PFDN-4, or the presence or absence of a diagnostic presence of PFDN-4, and the relative efficacy of one or another anti-cancer agent. Such analyses can be performed, e.g., retrospectively, i.e., by detecting PFDN-4 levels in samples taken previously from patients that have subsequently undergone one or more types of anti-cancer therapy, and correlating the PFDN-4 levels with the known efficacy of the treatment.

Administration of Pharmaceutical and Vaccine Compositions

Inhibitors of PFDN-4 can be administered to a patient for the treatment of cancer, e.g., ovarian cancer. As described in detail below, the inhibitors are administered in any suitable manner, optionally with pharmaceutically acceptable carriers.

The identified inhibitors can be administered to a patient at therapeutically effective doses to prevent, treat, or control cancer. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular PFDN-4 inhibitors employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Inhibitors of Gene Expression

In one aspect of the present invention, PFDN-4 inhibitors can also comprise nucleic acid molecules that inhibit expression of PFDN-4. Conventional viral and non-viral based gene transfer methods can be used to introduce nucleic acids encoding engineered PFDN-4 polypeptides in mammalian cells or target tissues, or alternatively, nucleic acids e.g., inhibitors of PFDN-4 activity, such as siRNAs, ribozymes, or anti-sense RNAs. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11: 162-166 (1993); Dillon, *TIBTECH* 11: 167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds) (1995); and Yu et al., *Gene Therapy* 1: 13-26 (1994).

In some embodiments, siRNAs are administered. siRNA therapy is carried out by administering to a patient a siRNA by standard vectors encoding the siRNAs of the invention and/or gene delivery systems such as by delivering the synthetic siRNA molecules. Typically, synthetic siRNA molecules are chemically stabilized to prevent nuclease degradation in vivo. Methods for preparing chemically stabilized RNA molecules are well known in the art. Typically, such molecules comprise modified backbones and nucleotides to prevent the action of ribonucleases. Other modifications are also possible, for example, cholesterol-conjugated siRNAs have shown improved pharmacological properties (see, e.g., Song et al. *Nature Med.* 9:347-351 (2003).

Non-viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Methods

The use of RNA or DNA viral based systems for the delivery of inhibitors of PFDN-4 are known in the art. Conventional viral based systems for the delivery of PFDN-4 nucleic acid inhibitors can include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., a pancreas or breast tissue. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with PFDN-4 inhibitor nucleic acids and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

In some embodiments, PFDN-4 polypeptides and polynucleotides can also be administered as vaccine compositions to stimulate an immune response, typically a cellular (CTL and/or HTL) response. Such vaccine compositions can include, e.g., lipidated peptides (see, e.g.,Vitiello, A. et al., *J. Clin. Invest.* 95:341 (1995)), peptide compositions encapsulated in poly(DL-lactide-co-glycolide) ("PLG") microspheres (see, e.g., Eldridge, et al., *Molec. Immunol.* 28:287-294, (1991); Alonso et al., *Vaccine* 12:299-306 (1994); Jones et al., *Vaccine* 13:675-681 (1995)), peptide compositions contained in immune stimulating complexes (ISCOMS) (see, e.g., Takahashi et al., *Nature* 344:873-875 (1990); Hu et al., *Clin Exp Immunol.* 113:235-243 (1998)), multiple antigen peptide systems (MAPs) (see, e.g., Tam, *Proc. Natl. Acad. Sci. U.S.A.* 85:5409-5413 (1988); Tam, *J. Immunol. Methods* 196:17-32 (1996)), peptides formulated as multivalent peptides; peptides for use in ballistic delivery systems, typically crystallized peptides, viral delivery vectors (Perkus, et al., In: *Concepts in vaccine development* (Kaufmann, ed., p. 379, 1996); Chakrabarti, et al., *Nature* 320:535 (1986); Hu et al., *Nature* 320:537 (1986); Kieny, et al., *AIDS Bio/Technology* 4:790 (1986); Top et al., *J. Infect. Dis.* 124:148 (1971); Chanda et al., *Virology* 175:535 (1990)), particles of viral or synthetic origin (see, e.g., Kofler et al., *J. Immunol. Methods.* 192:25 (1996); Eldridge et al., *Sem. Hematol.* 30:16 (1993); Falo et al., *Nature Med.* 7:649 (1995)), adjuvants (Warren et al., *Annu. Rev. Immunol.* 4:369 (1986); Gupta et al., *Vaccine* 11:293 (1993)), liposomes (Reddy et al., *J. Immunol.* 148:1585 (1992); Rock, *Immunol. Today* 17:131 (1996)), or, naked or particle absorbed cDNA (Ulmer, et al., *Science* 259:1745 (1993); Robinson et al., *Vaccine* 11:957 (1993); Shiver et al., In: *Concepts in vaccine development* (Kaufmann, ed., p. 423, 1996); Cease & Berzofsky, *Annu. Rev. Immunol.* 12:923 (1994) and Eldridge et al., *Sem. Hematol.* 30:16 (1993)). Toxin-targeted delivery technologies, also known as receptor mediated targeting, such as those of Avant Immunotherapeutics, Inc. (Needham, Mass.) may also be used.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, cancer-specific nucleic acids or antibodies, hybridization probes and/or primers, antisense polynucleotides, siRNAs, ribozymes, dominant negative cancer polypeptides or polynucleotides, small molecules inhibitors of cancer-associated sequences etc. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of PFDN-4 cancer-associated sequences. Such kits can be prepared from readily available materials and reagents. For example, such kits can comprise one or more of the following materials: a PFDN-4 cancer-associated polypeptide or polynucleotide, reaction tubes, and instructions for testing PFDN-4 cancer-associated activity. Optionally, the kit contains biologically active PFDN-4 cancer protein. A wide variety of kits and components can be prepared according to the present invention, depending upon the intended user of the kit and the particular needs of the user. Diagnosis would typically involve evaluation of a plurality of genes or products. The genes will be selected based on correlations with important parameters in disease which may be identified in historical or outcome data.

EXAMPLES

Array Comparative Genome Hybridization (aCGH) was used to evaluate pancreatic islet cell tumors from RIP1-Tag2 transgenic mice. RIP1-Tag2 mice express an oncogene, the SV40 large T antigen, that interferes with the functions of the Rb and p53 tumor suppressors. This is necessary, but not sufficient to elicit tumors, in that tumorigenesis takes 12 weeks and involves the sequential appearance of histological stages inferred to involve genetic and epigenetic secondary events that facilitate tumor progression.

Array CGH data using RIP-Tag2 tumors identified a recurrent copy number gain in chromosome 2, cytoband H3 with a frequency of 15-30% of tumors, depending on genetic background (Hager et al, 2003). This locus is of particular interest because it is syntenic to human 20q13.2, a region frequently amplified in a variety of human cancers, including pancreatic endocrine tumors (Stumpf 2000, Zhao 2001). In human cancers, amplifications of this locus are associated with a more aggressive phenotype, increased metastasis and poor clinical prognosis (Hidaka 2000, Tanner 1995, Diebold 2000).

Detailed genomic studies of human tumors have revealed a high degree of genomic complexity in this amplicon (Collins 1998, Albertson 2000, Collins 2001).

The minimal region of amplification was defined by one tumor that had a very narrow gain of about 217 Kb, which contains BCAS1/NABC1, Cyp24, Prefoldin 4 (PFDN-4) and a putative pseudogene Ub16/SUMO. The broader region of recurrent gain encompasses the distal ~20Mb of mouse chromosome 2—and includes the mouse homolog of zinc-finger protein 217 (Znf217), a candidate oncogene that maps within the amplicon identified in human tumors.

Expression of all of the candidate genes and putative pseudogenes mapping within the locus commonly gained/amplified in RIP-Tag mouse and human breast tumors was assessed. Expression was analyzed using pools of tumors and different cell lines derived from these tumors (βTC cells). It was found that the PFDN-4 gene was consistently upregulated (FIG. 1A).

Of the genes in the amplified region, BCAS1, Cyp24 and 2 pseudogenes were excluded, as they were not expressed in primary tumors or in any islet tumor-derived PTC cell line (Table 1). Two genes were expressed in both tumors and βTC lines: the mouse homolog of Znf217 and PFDN-4. Of these two candidates, Znf217 was expressed in some, but not all βTC cell lines, and its expression levels did not correlate with the presence of amplification of mouse chromosome: some non-CNG2 cell lines showed higher expression levels than the CNG2-containing cell line βTC4 (not shown). On the other hand, PFDN-4 was expressed in all tumors and βTC cells tested, and its expression levels correlated with the presence of CNG2 (in βTC4 its expression levels were 2-2.5 higher than in the other βTC cell lines).

TABLE 1

EVALUATION OF CANDIDATE GENES IN THE REGION OF CNG2

| Gene | Within minimal CNG2? | Expressed in primary tumors? | Expressed in βTC? | Notes |
|---|---|---|---|---|
| PFDN-4 | Yes | Yes | All | Increased expression correlates with presence of CNG2 |
| BCAS | Yes | No | No | |
| Cyp24 | Yes | No | No | |
| DOK5 | ~225 kb distal | Yes | All | Control gene outside of the CNG2 locus |
| ZNF217 | ~200 kb proximal | Yes | Some | Candidate in human 20q13 amplicon |

PFDN-4 is one of six component proteins that comprises the Prefoldin prechaperonin complex that contributes to the folding of certain newly synthesized proteins, most notably actin and tubulin, major components of the cellular cytoskeleton. Quantitative RT-PCR analysis of the six Prefoldin subunit genes in an islet tumor-derived cell line lacking mouse chromosome 2 aberrations showed PFDN-4 to be expressed at much lower levels than the five prefoldin subunit genes (FIG. 1B), suggesting it might be limiting Prefoldin activity in normal islet β cells in tumors that do not contain an amplification of the chromosome.

Figure 2:
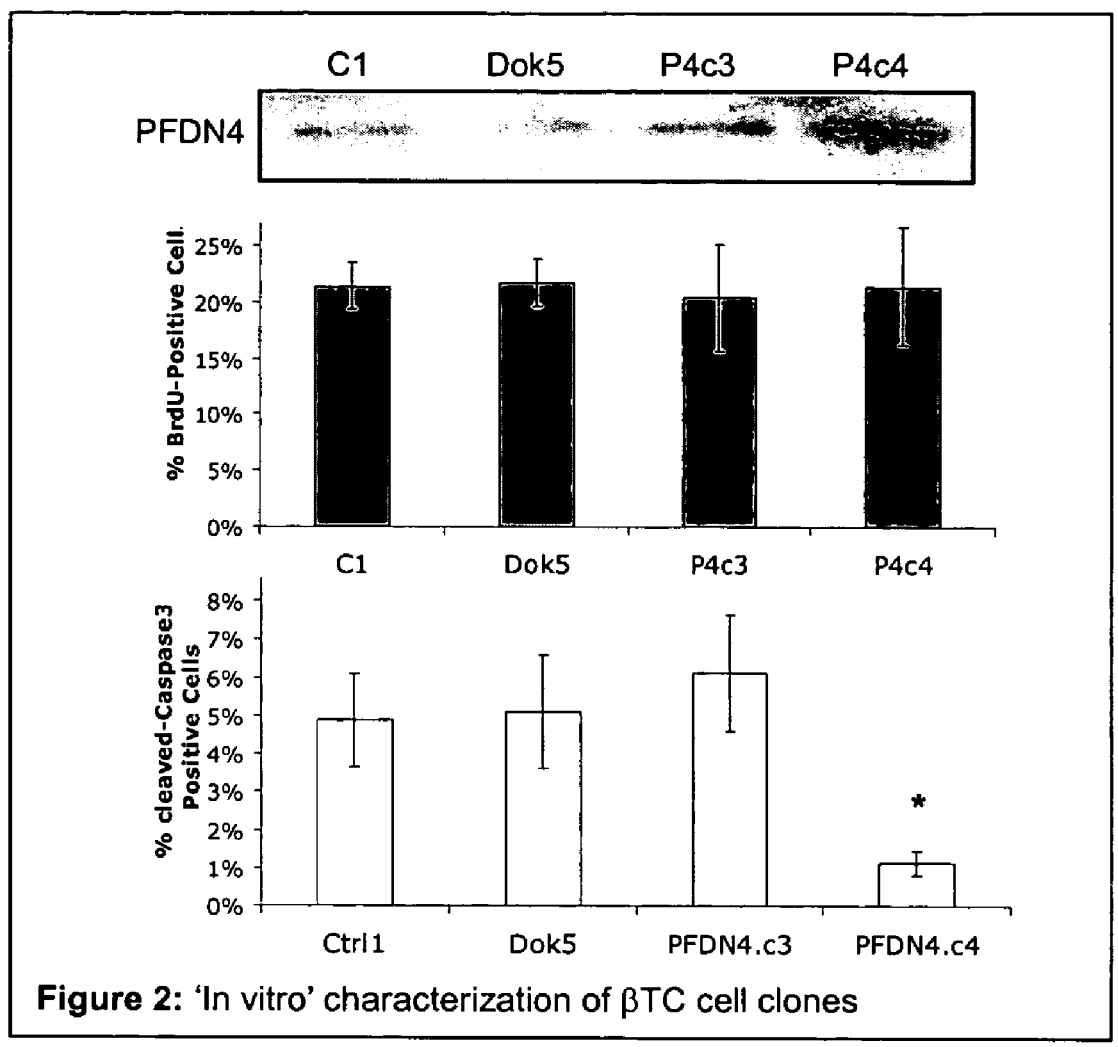
FIG. 2 provides exemplary data showing characterization of βTC cell clones overexpressing PFDN-4 (Low, P4c3; high, P4c4) compared to controls (empty vector, C1; cells overexpressing a linked gene, Dok4). Top, western blot for PFDN-4 levels is shown. Percentages of proliferating cells were determined by BrdU incorporation while apoptosis rates were determined by cleaved caspase-3 immunodetection. *, $p<0.001$.
Figure 3:
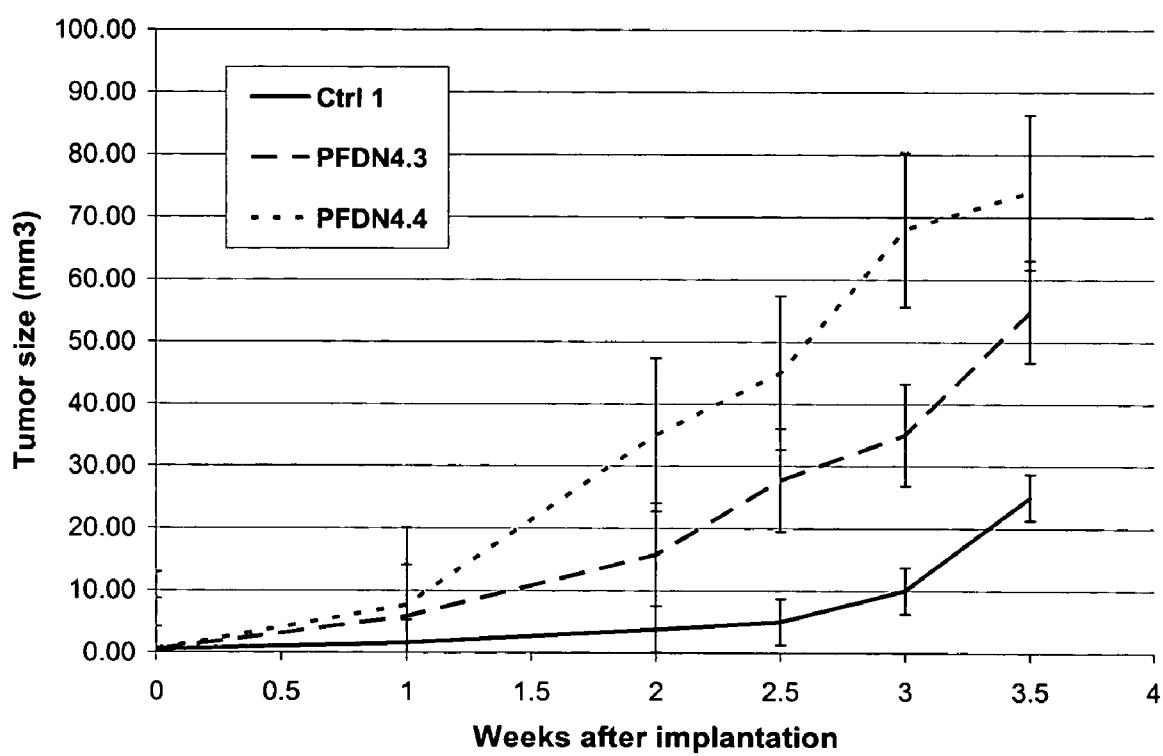
FIG. 3 provides exemplary data showing tumor growth of two βTC cell lines overexpressing PFDN-4 by 10× and 50× compared with empty vector cell line. Tumor size was measured with a caliper and the volume of a spheroid was calculated in cubic millimeters.

To further investigate PFDN-4 as the affected oncogene/tumor progression factor in this locus, a series of transfected cultured βTC cell lines lacking mouse chromosome 2 amplification that expressed distinctively elevated levels of PFDN-4 were developed. Two control cell lines were also produced to complement the parental cell line. One control cell line carried an empty expression vector, while the other overexpressed DOK5, a gene on chromosome 2 that is 225 Kb distal to the region of amplification. DOK5 was included as a control because it is amplified in some tumors with large-scale gains but is arguably not the candidate oncogene by virtue of its exclusion in the minimal region. TaqMan® quantitative RT-PCR analysis showed that the DOK5-transfectant and one of the PFDN-4 transfectant clones (PFDN-4 clone3) overexpressed their respective gene ~50 fold compared to the basal parental and control cell lines; another PFDN-4-transfectant clone (PFDN-4 clone4) overexpressed to 10 fold levels compared to the parental and control cell lines. We assayed these cell lines both in vitro (FIG. 2) and via subcutaneous inoculation into immunodeficient Rag1-null mice to assess transplantation tumorigenicity (FIG. 3).

The cell culture studies with thee cell lines did not reveal any difference in proliferation rates (scored as cells in S-phase pulse labeled with BrdU) as a consequence of over-expressing either PFDN-4 or DOK5 (not shown). However, the PFDN-4-expressing cells had a 3-5 fold decrease in apoptosis rates in culture, scored as cleaved-Caspase-3 positively stained. DOK5 had not effect on either proliferation rate or frequency of apoptosis. The cell lines were also analyzed for the ability to grow in anchorage independent conditions in soft agar. The high expressing PFDN-4 line produced more abundant and large colonies, which is consistent with a more highly transformed phenotype.

In addition to having a reduced frequency of apoptosis, PFDN-4 over-expressing tumor cells also exhibiteds alterations in cell shape and cytoskeleton in culture, assuming a morphology suggestive of an epithelial to mesenchymal transition, a hallmark of increased malignancy in progression of many carcinomas. Moreover, when assayed for transplantation tumorigenicity, the PFDN-4-overexpressing cells showed a significant increase in tumor 'take' and tumor growth rate when injected subcutaneously into Rag1-knockout mice, as compared to non-transfected βTC lines, empty vector containing line, and the DOK5-overexpressing line, as summarized in Table 2 and FIG. 1, and from additional data not shown. As shown in FIG. 3, both PFDN-4-overexpressing clones formned palpable tumors with a shorter latency and evidenced a faster rate of tumor growth than control cells from the βTC line transfected with the empty vector.

TABLE 2

| Cell Line | Over-expressing? | # cells inoc. s.c. into ear? | Tumor take rate (tumors/mice inj.) |
|---|---|---|---|
| βTC-vector | Empty vector,/n.a. | 1 $10^6$ | 4/9 |
| βTC-PFDN4.4 | 10X-PFDN-4 | 1 $10^6$ | 12/12 |
| βTC-PFDN4.3 | 50X-PFDN-4 | 1 $10^6$ | 8/9 |
| βTC-DOK5 | 50X-DOK5 | 1 $10^6$ | 1/2 |

We also evaluated microarray profiling data on a series of human breast cancer cell lines that were genotyped for copy number at chromosome 20q13 (FIG. 4). This analysis showed a correlation between increased copy number of the 20q13 locus and increased expression of PFDN-4.

As noted above, the CNG2 locus is syntenic to human 20q13 locus that is frequently amplified in human cancers. To test the hypothesis that PFDN-4 is also playing an important role in human tumors, we performed an 'in silico' analysis of PFDN-4 expression levels in a publicly-available human tumor expression arrays (Ramaswamy et al., *Proc. Natl. Acad. Sci USA* 98:15149-15154). This dataset consists of a tumor bank with normal control tissue from 14 different tissues of origin ranging from epithelial tumors, mesenchimal tumors and lymphatic malignancies. Consistent with the findings in RIP-Tag2 mouse model, expression levels of PFDN-4 were significantly higher in the tumor samples compared to control samples (pooled all 218 tumor samples versus pooled all 90 normal tissues, p=0.001). Moreover, several tissues showed significant increases in PFDN-4 levels in the tumors. These included: breast adenocarcinoma (p=0.02), uterus adenoma (p=0.03), mesothelioma (p=0.02), and follicular lymphoma (p<0.001). In another dataset from the same laboratory (Bhattacharjee, et al., *Proc. Natl. Acad. Sci USA* 98:13790-13795, 2001), significant differences were found in 190 lung adenocarcinoma samples and 21 squamous carcinoma samples when compared to 17 normal tissue samples (p=0.009 and p<0.001 respectively).

The data collectively implicate PFDN-4 as an important oncogene/tumor progression factor underlying the recurrent copy number gains of the CNG2 locus and as playing a role in human malignancies.

The above examples are provided by way of illustration only and not by way of limitation. Those of skill in the art will readily recognize a variety of noncritical parameters that could be changed or modified to yield essentially similar results.

All publications and patent applications cited in this specification are herein incorporated by reference as if each individual publication or patent application were specifically and individually indicated to be incorporated by reference.

Table of Exemplary Sequences

```
SEQ ID NO:1 Human prefoldin 4 polynucleotide
sequence--cds 19-423 Accession number BC010953.1
    1 ggggagtcca gtcccaagat ggcggccacc atgaagaagg
      cggctgcaga agatgtcaat 61 gttactttcg aagatcaaca aaagataaac aaatttgcac
      ggaatacaag tagaatcaca 121 gagctgaagg aagaaataga agtaaaaaag aaacaactcc
      aaaacctaga agatgcttgt 181 gatgacatca tgcttgcaga tgatgattgc ttaatgatac
      cttatcaaat tggtgatgtc 241 ttcattagcc attctcaaga agaaacgcaa gaaatgttag
      aagaagcaaa gaaaaatttg 301 caagaagaaa ttgacgcctt agaatccaga gtggaatcaa
      ttcagcgagt gttagcagat 361 ttgaaagttc agttgtatgc aaaattcggg agcaacataa
      accttgaagc tgatgaaagt 421 taaacatttt ataatacttt ttttatttgt ttaataaact
      tgaatattgt aaaaaaaaaa 481 aaaaaaaaaa aaaaaaaaaa SEQ ID NO:2 Human prefoldin 4 polypeptide
sequence; Accession number: Q9NQP4
MAATMKKAAAEDVNVTFEDQQKINKFARNTSRITELKEEIEVKKKQLQNL
EDACDDIMLADDDCLMIPYQIGDVFISHSQEETQEMLEEAKKNLQEEIDA
LESRVESIQRVLADLKVQLYAKFGSNINLEADES
```

---

What is claimed is:

1. A method of detecting cancer in a biological sample from a patient, the method comprising detecting an increase in the level of a polypeptide set forth in SEQ ID NO:2, relative to that in a non-cancer biological sample from the same tissue, thereby detecting the presence of cancer in the patient, wherein the cancer is selected from the group consisting of: pancreatic cancer, lung cancer, medulloblastoma, breast cancer, ovarian cancer, mesothelioma, gastric adenocarcinoma, uroepithelial cancer, pancreatic neuroendocrine cancer, and islet cell tumors.

2. The method of claim 1, wherein the step of detecting an increase in the level of the polypeptide comprises performing an immunoassay.

* * * * *